(12) United States Patent
Eramo

(10) Patent No.: US 7,547,474 B2
(45) Date of Patent: Jun. 16, 2009

(54) LUBRICIOUS COATINGS FOR PHARMACEUTICAL APPLICATIONS

(75) Inventor: Lincoln Eramo, Winchester, CA (US)

(73) Assignee: Med-eez, Inc., Palm Desert, CA (US)

( * ) Notice: Subject to any disclaimer, the term of this patent is extended or adjusted under 35 U.S.C. 154(b) by 89 days.

(21) Appl. No.: 11/405,991

(22) Filed: Apr. 17, 2006

(65) Prior Publication Data

US 2007/0243246 A1    Oct. 18, 2007

Related U.S. Application Data

(63) Continuation-in-part of application No. 11/400,092, filed on Apr. 6, 2006, now abandoned.

(51) Int. Cl.
*B32B 5/66* (2006.01)

(52) U.S. Cl. .................. 428/403; 428/407; 427/212; 424/474; 424/475; 424/482

(58) Field of Classification Search ................ 428/403, 428/407; 427/212; 424/474, 475, 482
See application file for complete search history.

(56) References Cited

U.S. PATENT DOCUMENTS

| | | | | |
|---|---|---|---|---|
| 5,693,034 | A * | 12/1997 | Buscemi et al. | 604/265 |
| 6,485,747 | B1 * | 11/2002 | Flanagan et al. | 424/479 |
| 6,506,823 | B2 * | 1/2003 | Burns et al. | 524/35 |
| 2005/0054774 | A1 | 3/2005 | Kangas | 525/123 |
| 2005/0055044 | A1 | 3/2005 | Kangas | 606/194 |
| 2005/0170071 | A1 | 8/2005 | Eramo | 427/2.1 |

* cited by examiner

*Primary Examiner*—Leszek Kiliman
(74) *Attorney, Agent, or Firm*—DLA Piper LLP (US)

(57) ABSTRACT

The invention provides pills and tablets having lubricious coating deposited over the outer surface of the pills and the tablets.

47 Claims, 1 Drawing Sheet

LUBRICIOUS COATINGS FOR PHARMACEUTICAL APPLICATIONS

CROSS-REFERENCE TO RELATED APPLICATION

The present application is a continuation-in-part application of, and claims priority under 35 U.S.C. § 120 to, the U.S. patent application Ser. No. 11/400,092, filed on Apr. 6, 2006, now abandoned the entire disclosure of which is incorporated herein by reference.

FIELD OF THE INVENTION

The present invention relates generally to manufacturing pharmaceutical articles and more specifically to methods of making such articles having a lubricious coating formed over the outer surfaces of the article.

BACKGROUND

Pills and tablets are widely used for administering drugs or other therapeutically beneficial substances to people and animals. Currently, the outer surface of many pills and tablets is quite rough creating difficulties for many patients, including persons having dysphagia (including) a pronounced gag reflex, as well as for many infants, children, adolescents, older persons (e.g., geriatric patients) and others. It is currently advisable to use water when taking most pills and tablets which creates difficulties in some situations, for example, when water is not available.

It is, therefore, desirable to have pills and tablets that are easy to swallow, which are appropriate for patients of any age and physical or mental conditions, and which can be administered without use of water. Previously, such products have not been provided. The present application provides such easy-to-swallow pills and tablets and methods for fabricating such products.

SUMMARY

According to one embodiment of the present invention, a pharmaceutical article is provided, including a substrate comprised of a therapeutically active agent, and a lubricious coating deposited over the substrate, wherein the article is adapted for swallowing by a mammalian subject, and wherein the coating is formed of a polymeric composition comprising a hydrophilic polymer and a cross-linked polymer, and wherein the lubriciousness of the coating is between 2 and 10 times better than the lubriciousness of a standard pill coating.

According to another embodiment of the present invention, the hydrophilic polymer can have a solubility parameter that is higher than about 8.5 $(cal/cm3)^{1/2}$, and the cross-linked polymer can be formed by polymerization of a cross-linkable monomer, selected from an acrylate, a methacrylate, an epoxy-acrylate, and isocyanates.

According to yet another embodiment, methods for fabricating the lubricious coatings described above are also provided.

According to yet another embodiment of the present invention, the pharmaceutical articles can be administered to humans including adolescents, children, infants, geriatric patients, and persons is suffering from dysphagia (including those having a pronounced gag reflex), as well as to animals.

DETAILED DESCRIPTION

Figure 1:
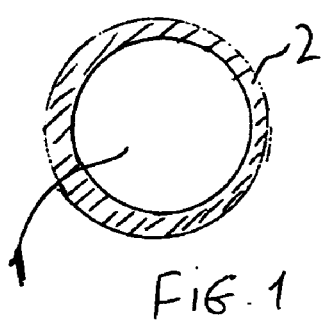
FIG. 1 illustrates schematically a cross section of a pharmaceutical article coated with a lubricious coating according to one embodiment of the invention.

The following are the definitions of some terms as used in the present application. If the terms and definitions provided below are inconsistent in any way with their generally accepted meanings, then, to the extent of such potential inconsistencies, the meanings provided below prevail.

The term "a therapeutically active agent" is defined as a compound or a substance which, when administered to a mammal in need thereof, may elicit a beneficial therapeutic response. The term "a therapeutically active agent" is inclusive of synthetic drugs, naturally occurring remedies, prescription drugs, over-the-counter drugs, generic drugs, brand-name drugs, vitamins, minerals, nutritional supplements, homeopathic remedies, herbal remedies and like items.

The terms "lubricious" and "lubriciousness" refer to objects having smooth, sleek or slippery surfaces. For the purposes of the present invention, the terms "lubricious" and "lubriciousness" are defined by the swallowability of a pill or a tablet. The pill or the tablet is considered "lubricious" if it is 2 to 10 times easier swallowed compared to the "egg-shell coated" pill as the term the "egg-shell coated" is understood in the art.

The term "a mammalian subject" refers to both humans and to warm blooded animals, such as domestic animals, e.g., cats and dogs, and farm animals, e.g., cattle, pigs, goats and sheep.

The term "dysphagia" refers to difficulty in swallowing, which can be associated, among other causes, with nerve damage due to neurological illness such as stroke, MS or Parkinson's disease.

The term "an adolescent" is defined as a human person whose age is between about 12 years and about 16 years.

The term "a child" is defined as a human person whose age is between about 2 years and about 12 years.

The term "an infant" is defined as a human person whose age is between about 1 day and about 2 years.

The term "a geriatric patient" is defined as a human person who has developed physical or mental disorders commonly associated with advanced age.

The term "gag reflex" is defined as a reflex contraction of the back of the throat that expels objects entering the throat, except those entering the throat as part of normal swallowing.

The term "a pill" is defined as a dose of a product that comprises a therapeutically active agent, in the form of a small pellet.

The term "a tablet" is defined as a dose of a product that comprises a therapeutically active agent, in the form of a small flat compressed block.

The term "spherical" is defined as the shape of a body of revolution generated by rotating a circle about a diameter.

The term "elliptical" is defined as the shape of a body of which all plane sections are either ellipses or circles.

The term "oblate spherical" is defined as the shape of a body of revolution generated by rotating an ellipse about its minor axis.

The term "prolate spherical" is defined as the shape of a body of revolution generated by rotating an ellipse about its major axis.

The term "right circular cylindrical" is defined as the shape of a body having two parallel circular bases, the distance between which defines the height of the body, and a wall of constant circular cross-section.

The term "discal" refers to a body having the right circular cylindrical shape, the height of which is not more than about 10% of its diameter.

The term "plano-convex" is defined as an object having two opposing surfaces of which one surface is flat or planar, and the other surface is convex. The term "convex" refers to the shape that is arched, curved, broadly obtuse, or equally rounded outward like the exterior of a sphere or circle.

The term "lenticular" is defined as an object having the shape of a double-convex lens.

The term "pyramidal" is defined as an object having the shape of a pyramid, including any kind of a regular pyramid or a truncated pyramid.

The term "conical" is defined as an object having the shape of a cone, including any kind of a regular cone or a frustum cone.

The term "ogival" is defined as an object having the shape of an ogive, i.e., a geometrical form resembling a bullet resulting from the intersection of two curves having the same radius of curvature.

The terms "cubical" and "cuboidal" are defined as objects having the shape of a cube and of a rectangular parallelepiped, respectively.

The term "hydrophilic polymer" is defined below in the application.

The term "monomer," in accordance with the definition adopted by the International Union of Pure and Applied Chemistry (IUPAC), refers to a molecule which can undergo polymerization thereby contributing constitutional units to the essential structure of a macromolecule (a polymer).

The term "polymer" is defined as being inclusive of homopolymers, copolymers, and oligomers. The term "homopolymer" is defined as a polymer derived from a single species of monomer. The term "copolymer" is defined as a polymer derived from more than one species of monomer, including copolymers that are obtained by copolymerization of two monomer species, those obtained from three monomers species ("terpolymers"), those obtained from four monomers species ("quaterpolymers"), etc. The term "oligomer" is defined as a low molecular weight polymer in which the number of repeating units does not exceed twenty.

The term "copolymer" is further defined as being inclusive of random copolymers, alternating copolymers, graft copolymers, and block copolymers. The term "random copolymer" is defined as a copolymer comprising macromolecules in which the probability of finding a given monomeric unit at any given site in the chain is independent of the nature of the adjacent units. In a random copolymer, the sequence distribution of monomeric units follows Bernoullian statistics. The term "alternating copolymer" is defined as a copolymer comprising macromolecules that include two species of monomeric units in alternating sequence.

The term "cross-linking" refers to a process of establishment of chemical links between chains of molecules of a polymer, resulting in a single tridimensional network that has greater strength and less solubility compared to the non-cross-linked polymer.

The term "interpenetrating network," in accordance with the definition adopted by the IUPAC, refers to a polymeric system comprising two or more networks which are at least partially interlaced on a molecular scale, to form both chemical and physical bonds between the networks. The networks of an IPN cannot be separated unless chemical bonds are broken. In other words, an IPN structure represents two or more polymer networks that are partially chemically cross-linked and partially physically entangled.

The term "initiator," in accordance with the definition adopted by the IUPAC, refers to a substance introduced into a reaction system in order to bring about reaction or process generating free radicals or some other reactive reaction intermediates which then induce a chain reaction.

The term "photoinitiator," in accordance with the definition adopted by the IUPAC, refers to a substance capable of inducing the polymerization of a monomer by a free radical or ionic chain reaction initiated by photoexcitation.

The terms "acrylic," "polyacrylic," "acrylate," or "polyacrylate" refer to a product that is inclusive of a monomer, oligomer, pre-polymer and polymer, as applicable, having at least one acrylic moiety (I) or methacrylic moiety (II), or derived from a product having at least one acrylic moiety (I) or methacrylic moiety (II):

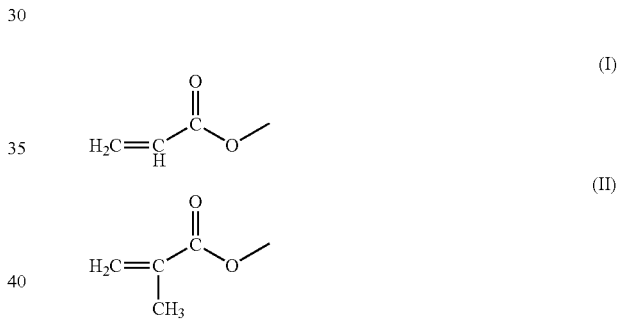

The terms "epoxy-acrylate" and "poly(epoxy-acrylate)" refer to a product that is inclusive of a monomer, oligomer, pre-polymer and polymer, as applicable, having at least one oxirane ring (III) (epoxide ring) that has been reacted and given acrylic functionality

According to embodiments of the invention, lubricious pharmaceutical articles are provided. The pharmaceutical articles comprise a pharmaceutical item, such as a pill or a tablet, coated with a polymeric coating making the article lubricious and, consequently, easy to swallow.

Figure 2:
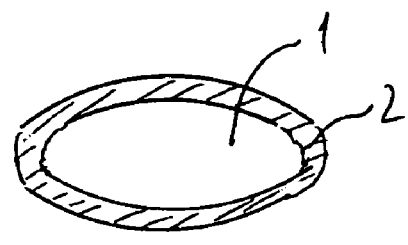
FIG. 2 illustrates schematically a cross section of a pharmaceutical article coated with a lubricious coating according to another embodiment of the invention.
Figure 3:
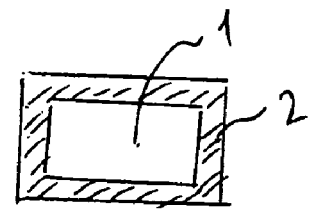
FIG. 3 illustrates schematically a cross section of a pharmaceutical article coated with a lubricious coating according to yet another embodiment of the invention.
Figure 4:
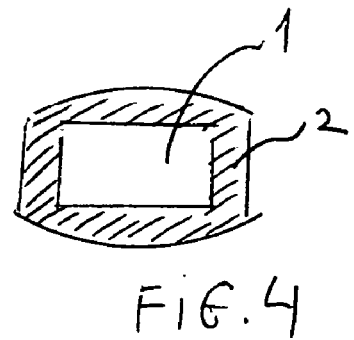
FIG. 4 illustrates schematically a cross section of a pharmaceutical article coated with a lubricious coating according to another embodiment of the invention.

The pharmaceutical items can include a substrate comprising any drug or any other therapeutically active substance, such as synthetic drugs, naturally occurring remedies, prescription drugs, over-the-counter drugs, generic drugs, brand-name drugs, vitamins, minerals, nutritional supplements, homeopathic remedies, or herbal remedies, wherein the substrate has been shaped as a pill or a tablet. With the reference to FIGS. 1-4, the pharmaceutical articles include a substrate I formed of therapeutically active substance and a layer of a lubricious coating 2 disposed over the substrate 1. The cross-section views of the items are shown on FIGS. 1-4. For illustrative purposes only, in a non-limiting way, the shape of the pharmaceutical articles that can be used include spherical (FIG. 1), elliptical (FIG. 2), cuboidal or discal (FIG. 3), and lenticular (FIG. 4).

There are no limitations on the shape of the pharmaceutical item, and additional shapes into which the pharmaceutical item can be shaped include also oblate spherical, prolate spherical, cylindrical (including right circular cylindrical), discal, convex (including plano-convex), pyramidal (including truncated pyramidal), conical (including frustoconical), and ogival shape. Those having ordinary skill in the art can determine the required shape and can devise a method of shaping the pharmaceutical item in any desired way. To manufacture the pharmaceutical articles, i.e., uncoated pharmaceutical articles, those having ordinary skill in the art can use commonly known manufacturing techniques and equipment adopted in the pharmaceutical industry.

To form the polymeric coating over the pharmaceutical item, according to embodiments of the present invention, a liquid polymer-containing composition can be prepared first. The composition can include at least two components and a solvent such as water. The first component includes at least one biologically compatible hydrophilic polymer. The second component includes at least one cross-linkable monomer or cross-linkable oligomer capable of forming a cross-linked polymer. Both the first component and the second component are discussed in detail later in the application.

The polymeric coating can be then formed on the outer surface of the pharmaceutical item that has been shaped in a desired way. One method of applying the coating can be spraying a liquid solvent- or water-based polymer-containing composition over the pharmaceutical item. A tablet pan sprayer or other commonly used equipment can be utilized. Alternatively, other coating methods can be employed, for example, spin coating or vapor deposition method. Those having ordinary skill in the art can select the appropriate coating method, taking into account the nature of the polymer in the coating and the desired thickness of the ultimate polymeric coating.

The liquid polymer-containing composition deposited over the pharmaceutical item can then be processed to form the ultimate dry coating. The processing steps include drying (i.e., the removal of the solvent or water from the liquid polymer-containing composition) and polymerizing the cross-linkable monomer or cross-linkable oligomer. Those having ordinary skill in the art can select the appropriate method to be used for the polymerization of the cross-linkable monomer or the cross-linkable oligomer. One typical polymerization method that can be used is ultraviolet light-initiated polymerization. As a result of the processing steps, a dry lubricious coating can be formed over the pharmaceutical item to provide the pharmaceutical article of the present invention. The thickness of the final dry coating can be between about 2.5 μm (0.1 mil) and about 25 μm (1 mil), such as between about 5 μm (0.2 mil) and about 12.5 μm (0.5 mil).

As mentioned above, the first polymeric component includes at least one biologically compatible hydrophilic polymer. Without being bound by a particular theory, it is submitted that the presence of a hydrophilic polymer(s) in the coating may be one factor that can facilitate the formation of the lubricious coating by providing the coating with the ability of being moisturized.

One example of a class of hydrophilic polymers from which a specific hydrophilic polymer(s) can be selected for use in the lubricious coatings of the present invention is the class of poly(alkylene glycols) and alkoxy poly(alkylene glycols). One poly(alkylene glycol) that can be used is poly(ethylene glycol)(PEG), also known as poly(ethylene oxide) (PEO) having the general structure H—[O—CH$_2$—CH$_2$]$_n$—OH, where n is an integer having value more than 2. The weight-averaged molecular weight of PEO that can be used can be between about 50,000 and 1,500,000 Daltons, for example, between about 100,000 and 1,000,000 Daltons, such as about 900,000 Daltons.

An example of another poly(alkylene glycol) that can be used is poly(propylene glycol)(PPG). Non-limiting examples of other classes of suitable biologically compatible hydrophilic polymers that can be used, either alone, or in any combination with PEG and/or PPG, include polymeric alcohols, e.g., poly(vinyl alcohol) and poly(N-vinyl lactams), such as poly(vinyl pyrrolidone).

Those having ordinary skill in the art may wish to select yet (an)other hydrophilic polymer(s) to be used in the lubricious coating of the present invention. In making their selection, those skilled artisans may be guided by understanding of the fact that for the purposes of the present invention a polymer is considered hydrophilic if it satisfies the hydrophilicity requirement described below.

The hydrophilicity of a polymer is closely related to its polarity. Indeed, polar substances are substances that have a dipole moment μ greater than 0 Debye. As a general rule, polar substances dissolve well in other polar substances, such as water. Accordingly, polar substances can be broadly categorized as "hydrophilic."

One method of defining the hydrophilicity of a polymer is by the Hildebrand solubility parameter δ of the polymer, as represented by equation 1 (see, "Polymer Handbook," 2$^{nd}$ Edition, Brandrup J. and E H Immergut, ed., Wiley-Interscience, John Wiley & Sons, N.Y. (1975)):

$$\delta = (\Delta E/V)^{1/2} \quad (1)$$

where δ is the solubility parameter of a polymer in (cal/cm$^3$)$^{1/2}$, ΔE is the theoretical energy of vaporization of the polymer (in calories), and V is the molar volume of the polymer (in cm$^3$).

Because polymers usually cannot be vaporized without decomposition, the solubility parameter is measured indirectly. Briefly, solvents in which a polymer dissolves without a change in heat or volume are identified. The solubility parameter of the polymer is then defined to be the same as the solubility parameters of the identified solvents.

As a general rule, the value of the solubility parameter δ is proportional to the degree of hydrophilicity of a polymer. Polymers that are very hydrophilic may have a high solubility parameter value. A polymer that is sufficiently hydrophilic for use in the lubricious coatings of the present invention can have a solubility parameter that is more than about 8.5 (cal/cm$^3$)$^{1/2}$, such as higher than about 10 (cal/cm$^3$)$^{1/2}$, for example, higher than about 11.5 (cal/cm$^3$)$^{1/2}$.

Table 1 illustrates the solubility parameters of various polymers. The data is available in the general literature on physical chemistry of polymers, and those having ordinary skill in the art can find the information on the values of the solubility parameters of various polymers in generally available technical references.

TABLE 1

Hildebrand Solubility Parameters for Selected Hydrophilic Polymers

| No. | Polymer | Hildebrand Solubility Parameter $\delta$, $(cal/cm^3)^{1/2}$ |
|---|---|---|
| 1 | Poly(isobutylene) | 16.2 |
| 2 | Poly(methylmethacrylate) | 18.6 |
| 3 | Poly(vinyl acetate) | 19.2 |
| 4 | Poly(hexamethylene adipamide) | 27.8 |
| 5 | Poly(styrene) | 9.1 |
| 6 | Poly(vinyl chloride) | 9.7 |
| 7 | Poly(vinylidene chloride) | 12.2 |
| 8 | Poly(ethylene terephthalate) | 10.7 |
| 9 | Poly(vinyl acetate) | 10.2 |

Accordingly, in addition to poly(alkylene glycols), poly(vinyl alcohol), and poly(N-vinyl lactams) described above, those having ordinary skill in the art can select at least one alternative hydrophilic polymer, so long as such alternative polymer(s) is(are) biologically compatible and has(have) the Hildebrand solubility parameter(s) within the above-described limits. Non-limiting examples of polymers from which the alternative polymer(s) can be selected include copolymers of methylvinyl ether and maleic acid, maleic anhydride polymers and copolymers, poly(acrylic acid), poly(methacrylic acid), polymers of hydroxyl-substituted lower alkylacrylates and alkylmethacrylates, such as poly(2-hydroxyalkyl acrylate) or poly(2-hydroxyalkylmethacrylate), polyamides, poly(acrylamides), poly(methacrylamides), poly(sodium-4-styrenesulfonates), poly(sodium vinylsulfonates), poly(3-hydroxybutyric acids), poly(urethanes), poly(ethyleneimines), polyurethane-polyether polymers, e.g., urethane-poly(ethylene oxide), poly(vinylsulfonic acid), heparin, dextran, dextan sulfate, and modified dextrans, poly(saccharides), chondroitin sulfate, lecithin and copolymers and mixtures thereof.

As mentioned above, the second component of the coating composition includes at least one cross-linkable monomer or a cross-linkable oligomer. Without being bound by a particular theory, it is submitted that the presence of a cross-linkable monomer(s) or cross-linkable oligomer(s) in the coating composition may lead to the formation of an interpenetrating polymer network which can include the above-discussed hydrophilic polymer(s). The interpenetrating network can help entrapping the hydrophilic polymer(s) on the surface of the pharmaceutical substrate being coated and thus can be one factor facilitating the formation of the lubricious coating.

Examples of suitable cross-linkable cross-linkable monomer(s) or cross-linkable oligomer(s) include acrylate, methacrylate, epoxy-acrylate, and isocyanate products. Those skilled in the art will select appropriate cross-linkable monomer(s) or cross-linkable oligomer(s) and will conduct the process of polymerization of such monomer(s) or oligomer(s). For the purposes of the present invention, an appropriate monomer or oligomer is a monomer or oligomer that is completely water soluble. Alternatively, in some embodiments, a monomer or an oligomer that is soluble in a mixture of water and a lower alcohol, such as ethanol or iso-propanol, can be also used.

For example, to obtain cross-linked poly(acrylate) or poly(methacrylate) polymer(s), such polymerizable monomer(s) or oligomer(s) as alkoxylated acrylates or alkoxylated methacrylates having at least two acrylate or methacrylate groups, respectively, can be used, for example, those having three or more acrylate or methacrylate groups. The degree of alkoxylation in the alkoxylated acrylates or alkoxylated methacrylates can be between about 1 and 20 moles, such as between about 2 and 20 moles, for example, between about 3 and about 20.

Those having ordinary skill in the art may find it desirable to use the alkoxylated acrylates or alkoxylated methacrylates having between about 2 and 18 moles of alkoxylation, for example, between about 3 and 15 moles of alkoxylation. Examples of suitable alkoxylate groups include both propoxylates and ethoxylates as well as mixtures thereof.

Examples of suitable bi-, tri-, tetra-, etc. polyfluctional alkoxylated or polyalkoxylated monomeric or oligomeric acrylates include alkoxylated, desirably ethoxylated or propoxylated, neopentyl glycol diacrylates, butanediol diacrylates, trimethylolpropane tri-acrylates glyceryl triacrylates; and combinations thereof.

In one embodiment, an alkoxylated trimethylol propane triacrylate monomer or oligomer can be utilized, such as an ethoxylated trimethylol propane triacrylate. Such compounds are available from Sartomer Company, Inc. of Exton, Pa. One example of such a compound is SR9035 having about 15 moles of ethoxylation and a molecular weight of 956 Daltons. Another example of such a compound is SR454 having about 3 moles of ethoxylation, a molecular weight of 454 Daltons and a water solubility of 15 mass %. Another example of such a compound is SR499 having about 6 moles of ethoxylation and a molecular weight of 560 Daltons. Yet another example of such a compound is SR502 having about 9 moles of ethoxylation and a molecular weight of 693 Daltons.

Other examples of suitable polymerizable alkoxylated acrylate and methacrylate monomers or oligomers include, but are not limited to, propoxylated trimethylol propane triacrylate, propoxylated trimethylol propane trimethacrylate, ethoxylated pentaerythritol tetraacrylate, ethoxylated pentaerythritol tetramethacrylate, propoxylated neopentyl glycol diacrylate, propoxylated glyceryl triacrylate, propoxylated glyceryl trimethacrylate, trimethylolpropane ethoxylate and methyl ether diacrylate.

The polymerizable monomers are typically polymerized through the exposure to radiation such as ultraviolet radiation, e-beam radiation, or laser beam radiation. The exposure time and the intensity of radiation can be determined by those having ordinary skill in the art, depending on the light source or initiator that is used. Many ethoxylated acrylate and ethoxylated methacrylate compounds can be polymerized via a free radical mechanism. They also may be sensitive to oxygen and can form stable radicals in its presence. Thus, it may be advantageous to employ an inert gas purge.

The above-mentioned process of polymerization and crosslinking may be facilitated by the addition of a small amount of a photoinitiator. Any photoinitiator which is suitable for use in free radical polymerization can be used. For example, those having ordinary skill in the art can select from such suitable photoinitiators as benzophenones, acrylated amine synergists, ketone type, i.e. aromatic-aliphatic ketone derivatives, including benzoin and its derivatives, benzil ketals, and α-amino ketones.

Some examples of specific photoinitiators that can be used include, but are not limited to, 2-phenyl-1-indanone, 1-hydroxylcyclohexylphenyl ketone such as IRGACURE 184 available from Ciba Specialty Chemicals, BENACURE184 available from Mayzo Co. and SARCURE SR1122 available from Sartomer Co., benzophenone such as BENACURE BP; benzil dimethyl ketal or 2,2'dimethoxy-2-phenylacetophenone such as BENACURE 651 and IRGACURE 651, 2-hydroxy-2-methyl-1-phenyl-1-propanone such as BENACURE 1173, 2-methyl 1-[4-methylthio)phenyl]2-morpholinopropan-1-one such as IRGACURE 907, and morpholinoketone such as IRGACURE 369, and blends thereof.

Examples of epoxy-acrylates that can be used include such commercially available products as EBICRYL 3200, EBICRYL 3700, EBICRYL 3701, available from Scytec Co., and Sartomer products, such as CN104 (a difunctional bisphenol A based epoxy acrylate), and similar epoxy acrylates CN UVE 151, CN 2102E, and CN 120J90.

Photoinitiators available commercially in a variety of blends can be also used. Examples of commercially available blends include, but are not limited to, a blend of 4-methylbenzophenone and benzophenone such as SARCURE SR1136, a blend of trimethylbenzophenone and methylbenzophenone such as SARCURE SR1137, and a blend of 1-hydroxylcyclohexylphenyl ketone and benzophenone such as BENACURE 500.

In addition to the above-discussed components that are used to form the lubricious coatings of the present invention, the coating compositions can also optionally include various additives and processing aids commonly used in the coating industry. For example, adhesion promoters (such as Silane 6020 available from Dow Chemicals Co.) or flow aids (such as Modaflow 3000 available from Surface Specialties Co.) can be so used.

The pharmaceutical articles fabricated as discussed above can be used with any kind of pharmaceutical substrate. The pharmaceutical articles can be administered to persons having difficulties swallowing (e.g., persons having a pronounce gag reflex), to children, infants, or geriatric patients. The pharmaceutical articles can be also administered to animals. In one embodiment, the pharmaceutical articles of the present invention are suitable for waterless administration.

The following examples are provided to further illustrate the advantages and features of the present invention, but are not intended to limit the scope of the invention.

EXAMPLE 1

Preparing a Poly(ethylene oxide)-Based Formulation for Coating a Pill

A coating composition was prepared, by mixing together the following components:

(a) about 2.00 mass % of poly(ethylene oxide) having the weight-averaged molecular weight of about 900,000 Daltons;

(b) about 0.8 mass % of the acrylic compound SR9035, obtained from Sartomer Co., the compound having about 15 moles of ethoxylation and a molecular weight of 956 Daltons;

(c) about 0.05 mass % of the flow aid Modaflow 3000, obtained from Surface Specialties Co.;

(d) about 0.025 mass % of the adhesion promoter Silane 6020, obtained from Dow Chemical Co.;

(e) about 0.0015 mass % of the photoinitiator 2-methyl 1-[4-methylthio)phenyl]2-morpholinopropan-1 (IRGACURE 907) obtained from Ciba Specialty Chemicals; and (f) the balance, de-ionized (by reverse osmosis) water.

The composition can then be applied onto a pill or a tablet, dried, and UV-cured to form a lubricious coating. The pill or the tablet can then be administered to a person or animal in need thereof.

EXAMPLE 2

Preparing a Poly(ethylene oxide)-Based Formulation Containing an Epoxy-Acrylate for Coating a Pill A coating composition was prepared, by mixing together the following components:

(a) about 20.0 mass % of de-ionized (by reverse osmosis) water;

(b) about 2.40 mass % of poly(ethylene oxide) having the weight-averaged molecular weight of about 900,000 Daltons;

(c) about 0.8 mass % of the epoxy-acrylic compound CN104, which is a Sartomer product described above;

(d) about 0.12 mass % of the polyether-polyurethane compound TECOGEL 2000, available from Thermedics Inc. of Woburn, Mass.;

(e) about 0.1 mass % of the melamine-formaldehyde compound RESIMINE 797, obtained from Monsanto Co.;

(f) about 0.05 mass % of Modaflow 3000, described above;

(g) about 0.025 mass % of Silane 6020, described above;

(h) about 0.0015 mass % of the photoinitiator IRGACURE 907 described above; and (i) the balance, iso-propanol.

The composition can then be applied onto a pill or a tablet, dried, and UV-cured to form a lubricious coating. The pill or the tablet can then be administered to a person or animal in need thereof.

EXAMPLE 3

Preparing a Poly(ethylene oxide)-Based Formulation Containing an Epoxy-Acrylate and Isocyanate for Coating a Pill A coating composition was prepared, by mixing together the following components:

(a) about 20.0 mass % of de-ionized (by reverse osmosis) water;

(b) about 2.40 mass % of poly(ethylene oxide) having the weight-averaged molecular weight of about 900,000 Daltons;

(c) about 0.8 mass % of the epoxy-acrylic compound SR-CN104, described above;

(d) about 0.15% of hexamethylene diisocyanate;

(d) about 0.12 mass % of the polyether-polyurethane compound TECOGEL 2000, described above;

(e) about 0.1 mass % of the melamine-formaldehyde compound RESIMINE 797, described above;

(f) about 0.05 mass % of Modaflow 3000, described above;

(g) about 0.025 mass % of Silane 6020, described above;

(h) about 0.0015 mass % of the photoinitiator IRGACURE 907 described above; and (i) the balance, iso-propanol.

The composition can then be applied onto a pill or a tablet, dried, and UV-cured to form a lubricious coating. The pill or the tablet can then be administered to a person or animal in need thereof.

Although the invention has been described with reference to the above examples, it will be understood that modifications and variations are encompassed within the spirit and scope of the invention. Accordingly, the invention is limited only by the following claims.

What is claimed is:

1. A pharmaceutical article, comprising:
   (a) a substrate comprised of a therapeutically active agent; and
   (b) a lubricious coating deposited over the substrate,
   wherein the article is adapted for swallowing by a mammalian subject, and wherein the coating is formed of an interpenetrating polymer network comprising a hydrophilic polymer entrapped on the surface of the substrate, and a cross-linked polymer,
   wherein the lubriciousness of the coating is between 2 and 10 times better than the lubriciousness of a standard pill coating, with the further proviso that after the subject has swallowed the article, the article is metabolized by the body of the subject, thereby bringing about a therapeutic benefit to the mammalian subject.

2. The pharmaceutical article of claim 1, wherein the hydrophilic polymer has a solubility parameter that is higher than about 8.5 $(cal/cm^3)^{1/2}$.

3. The pharmaceutical article of claim 2, wherein the hydrophilic polymer has a solubility parameter that is higher than about 10 $(cal/cm^3)^{1/2}$.

4. The pharmaceutical article of claim 2, wherein the hydrophilic polymer has a solubility parameter that is higher than about 11.5 $(cal/cm^3)^{1/2}$.

5. The pharmaceutical article of claim 1, wherein the hydrophilic polymer is selected from the group consisting of a poly(alkylene glycols), an alkoxy poly(alkylene glycol), poly(vinyl alcohol), urethane-poly(ethylene oxide), and poly(N-vinyl lactam).

6. The pharmaceutical article of claim 5, wherein the hydrophilic polymer is selected from the group consisting of poly(ethylene oxide), poly(propylene glycol), and poly(vinyl pyrrolidone).

7. The pharmaceutical article of claim 5, wherein the hydrophilic polymer is poly(ethylene oxide).

8. The pharmaceutical article of claim 1, wherein the cross-linked polymer is formed by polymerization of monomers selected from the group consisting of acrylate, methacrylate, epoxy-acrylate, and isocyanates.

9. The pharmaceutical article of claim 8, wherein the acrylate is selected from the group consisting of monomers having least two acrylate groups.

10. The pharmaceutical article of claim 8, wherein the acrylate is selected from the group consisting of monomers having least three acrylate groups.

11. The pharmaceutical article of claim 8, wherein the methacrylate is selected from the group consisting of monomers having least two methacrylate groups.

12. The pharmaceutical article of claim 8, wherein the methacrylate is selected from the group consisting of monomers having least three methacrylate groups.

13. The pharmaceutical article of claim 1, wherein the mammalian subject is a human.

14. The pharmaceutical article of claim 13, wherein the human is selected from a group consisting of an adolescent, a child, and an infant.

15. The pharmaceutical article of claim 13, wherein the human is a geriatric patient.

16. The pharmaceutical article of claim 13, wherein the human is suffering from the gag reflex.

17. The pharmaceutical article of claim 1, wherein the mammalian subject is an animal.

18. The pharmaceutical article of claim 1, wherein the administration of the article is accomplished without use of water.

19. The pharmaceutical article of claim 1, wherein the article is selected from a group consisting of a pill and a tablet.

20. The pharmaceutical article of claim 19, wherein the pill has the shape selected from the group consisting of spherical, elliptical, oblate spherical, prolate spherical, pyramidal, conical, and ogival shape.

21. The pharmaceutical article of claim 19, wherein the tablet has the shape selected from the group consisting of right circular cylindrical, discal, plano-convex, lenticular, cubical, and cuboidal shape.

22. The pharmaceutical article of claim 1, wherein the therapeutically active agent is selected from the group consisting of synthetic drugs, naturally occurring remedies, prescription drugs, over-the-counter drugs, generic drugs, brand-name drugs, vitamins, minerals, nutritional supplements, homeopathic remedies, or herbal remedies.

23. A kit comprising packaging material and the pharmaceutical article according to claim 1 contained within the packaging material, wherein the packaging material comprises a label which indicates that the pharmaceutical article can be used for swallowing.

24. A method for manufacturing the pharmaceutical article according to claim 1, comprising forming the substrate and depositing the polymer-containing composition over the outer surface of the substrate to form the lubricious coating thereby.

25. The method of claim 24, further comprising drying the lubricious coating.

26. The method of claim 25, further comprising curing the lubricious coating by exposing the lubricious coating to the ultraviolet radiation.

27. A pharmaceutical article, comprising:
   (a) a substrate comprised of a therapeutically active agent; and
   (b) a lubricious coating deposited over the substrate,
   wherein the article is selected from the group consisting of a pill and a tablet, and wherein the coating is formed of an interpenetrating polymer network comprising a hydrophilic polymer and a cross-linked polymer,
   wherein the lubriciousness of the coating is between 2 and 10 times better than the lubriciousness of a standard pill coating, with the further proviso that after the subject has swallowed the article, the article is metabolized by the body of the subject, thereby bringing about a therapeutic benefit to the mammalian subject.

28. The pharmaceutical article of claim 27, wherein the hydrophilic polymer has a solubility parameter that is higher than about 8.5 $(cal/cm^3)^{1/2}$.

29. The pharmaceutical article of claim 27, wherein the hydrophilic polymer is selected from the group consisting of a poly(alkylene glycols), an alkoxy poly(alkylene glycol), poly(vinyl alcohol), urethane-poly(ethylene oxide), and poly(N-vinyl lactam).

30. The pharmaceutical article of claim 27, wherein the cross-linked polymer is formed by polymerization of a monomer selected from the group consisting of acrylate, methacrylate, epoxy-acrylate, and isocyanates.

31. The pharmaceutical article of claim 27, wherein the mammalian subject is selected from the group consisting of a human and an animal.

32. The pharmaceutical article of claim 27, wherein the administration of the article is accomplished without use of water.

33. The pharmaceutical article of claim 27, wherein the therapeutically active agent is selected from the group consisting of synthetic drugs, naturally occurring remedies, prescription drugs, over-the-counter drugs, generic drugs, brand-name drugs, vitamins, minerals, nutritional supplements, homeopathic remedies, or herbal remedies.

34. A kit comprising packaging material and the pharmaceutical article according to claim 27 contained within the packaging material, wherein the packaging material comprises a label which indicates that the pharmaceutical article can be used for swallowing.

35. A method for manufacturing the pharmaceutical article according to claim 27, comprising forming the substrate and depositing the polymer-containing composition over the outer surface of the substrate to form the lubricious coating thereby.

36. The method of claim 35, further comprising drying the lubricious coating.

37. The method of claim 36, further comprising curing the lubricious coating by exposing the lubricious coating to the ultraviolet radiation.

38. A pharmaceutical article, comprising:
(a) a substrate comprised of a therapeutically active agent; and
(b) a lubricious coating deposited over the substrate,
wherein the article is adapted for swallowing by a mammalian subject, and wherein the coating is formed of a comprising a hydrophilic polymer and a cross-linked polymer that is formed by polymerization of a monomer selected from the group consisting of acrylate, methacrylate, epoxy-acrylate, and isocyanates, or a combination thereof,
with the further proviso that the acrylate is selected from the group consisting of monomers having at least two acrylate groups and the methacrylate is selected from the group consisting of monomers having at least two methacrylate groups,
wherein the lubriciousness of the coating is between 2 and 10 times better than the lubriciousness of a standard pill coating, with the further proviso that after the subject has swallowed the article, the article is metabolized by the body of the subject, thereby bringing about a therapeutic benefit to the mammalian subject.

39. The pharmaceutical article of claim 38, wherein the hydrophilic polymer has a solubility parameter that is higher than about 8.5 $(cal/cm^3)^{1/2}$.

40. The pharmaceutical article of claim 38, wherein the hydrophilic polymer is selected from the group consisting of a poly(alkylene glycols), an alkoxy poly(alkylene glycol), poly(vinyl alcohol), urethane-poly(ethylene oxide), and poly(N-vinyl lactam).

41. The pharmaceutical article of claim 40, wherein the hydrophilic polymer is selected from the group consisting of poly(ethylene oxide), poly(propylene glycol), and poly(vinyl pyrrolidone).

42. The pharmaceutical article of claim 38, wherein the article is selected from a group consisting of a pill and a tablet.

43. The pharmaceutical article of claim 38, wherein the therapeutically active agent is selected from the group consisting of synthetic drugs, naturally occurring remedies, prescription drugs, over-the-counter drugs, generic drugs, brand-name drugs, vitamins, minerals, nutritional supplements, homeopathic remedies, or herbal remedies.

44. A kit comprising packaging material and the pharmaceutical article according to claim 38 contained within the packaging material, wherein the packaging material comprises a label which indicates that the pharmaceutical article can be used for swallowing.

45. A method for manufacturing the pharmaceutical article according to claim 38, comprising forming the substrate and depositing the polymer-containing composition over the outer surface of the substrate to form the lubricious coating thereby.

46. The method of claim 45, further comprising drying the lubricious coating.

47. The method of claim 46, further comprising curing the lubricious coating by exposing the lubricious coating to the ultraviolet radiation.

* * * * *